(12) United States Patent
Masuo

(10) Patent No.: US 8,233,585 B2
(45) Date of Patent: Jul. 31, 2012

(54) X-RAY DIAGNOSTIC DEVICE

(75) Inventor: Katsuhiro Masuo, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 32 days.

(21) Appl. No.: 12/867,231

(22) PCT Filed: Apr. 14, 2008

(86) PCT No.: PCT/JP2008/057260
§ 371 (c)(1),
(2), (4) Date: Nov. 15, 2010

(87) PCT Pub. No.: WO2009/128129
PCT Pub. Date: Oct. 22, 2009

(65) Prior Publication Data
US 2011/0064187 A1    Mar. 17, 2011

(51) Int. Cl.
*A61B 6/00*    (2006.01)
(52) U.S. Cl. ............................... 378/4; 378/15
(58) Field of Classification Search ........................ 378/4
See application file for complete search history.

(56) References Cited

U.S. PATENT DOCUMENTS

| 3,500,778 | A | 3/1970 | Landoni | 112/118 |
| 7,042,975 | B2 * | 5/2006 | Heuscher | 378/8 |
| 7,653,172 | B2 * | 1/2010 | Harer et al. | 378/8 |
| 7,660,382 | B2 * | 2/2010 | Grass et al. | 378/8 |
| 7,711,083 | B2 * | 5/2010 | Heigl et al. | 378/20 |

FOREIGN PATENT DOCUMENTS

| JP | 62-186847 | 8/1987 |
| JP | 2001-120531 | 5/2001 |

* cited by examiner

*Primary Examiner* — Alexander H Taningco
(74) *Attorney, Agent, or Firm* — DLA Piper LLP (US)

(57) ABSTRACT

In a precessional operation where an X-ray irradiation means and a two-dimensional radiation detector are moving on a circular or elliptic orbit respectively by rotating either one of holding means, that is a C arm or a holding means at angular rate of a·sin(t) under a steady state condition and by rotating the other holding means at angular rate of b·cos(t), the operation is carried out at angular rate (f(t), g(t)) to ensure that the maximum acceleration is smaller than the steady state acceleration during a running-up period until steady is reached.

2 Claims, 5 Drawing Sheets

(a)

(b)

(a)

(b)

X-RAY DIAGNOSTIC DEVICE

TECHNICAL FIELD

The present invention relates to X-ray diagnostic device used for imaging and in particular to an art wherein moving images are collected while an X-ray irradiation means and an X-ray detection means, while kept opposing each other, engage in motion (precession) on a circular or elliptical orbit on different but parallel planes.

BACKGROUND ART

As shown in FIG. 8, an X-ray diagnostic device used for imaging of circulatory organs comprises: C-arm 103 which holds X-ray irradiation means 101 and X-ray image detection means 102 to oppose each other; holding means 104 which holds C-arm 103 so that the C-arm can slidingly rotate; holding means 105 which holds holding means 104 so that holding means 104 can rotate about the Y-axis (a horizontal axis that is orthogonal to the rotational axis about which the sliding rotation occurs); rotation driving means 113 that slidingly rotates C-arm 103; rotation driving means 114 that rotates holding means 104; and drive control means 106 that controls rotation driving means 113 and 114.

In an X-ray diagnostic device configured as afore-described, a known art for obtaining three-dimensional moving images is to rotate C-arm 103 with an angular velocity of a·sin(T) and to rotate holding means 104 with an angular velocity of b·cos(t) while X-ray irradiation means 101 and X-ray image detection means 102 are moved in a so-called precession motion on a circular or elliptical orbit on planes that are mutually parallel to each other (see for example Patent Reference 1).

Patent Reference 1: U.S. Pat. No. 3,500,778

DISCLOSURE OF THE INVENTION

Problems to be Solved by the Invention

With previous X-ray diagnostic device, even though the motion in a steady-state is either along a circular or an elliptical orbit, no consideration was given to the motion that occurs before a steady-state motion is reached.

FIG. 9 is a graph showing the rotational angular velocity of C-arm 103 and holding means A in previous X-ray diagnostic device. Time t is plotted along the horizontal axis, and angular velocity is plotted along the vertical axis. The rotational angular velocities of C-arm 103 and holding means A are trigonometric functions with a phase difference of $\pi/2$ maintained between each other. This means that the angular velocity of both of them is never 0 at the same time once a steady-state is reached. Since the C-arm 103 and holding means 104 carry a heavy object such as the X-ray irradiation means 101 or the X-ray image detection means 102, they cannot be instantaneously accelerated. Moreover, if they are rapidly accelerated, the whole system will vibrate. Not only can such vibrations create discomfort in the subject being imaged but the vibrations that are created during a run to a steady-state operation can remain even after a steady-state is reached, causing images that are continuously shot to shake.

Still furthermore, the area around the X-ray diagnostic device is occupied by external apparatuses such as the top board on which the subject being imaged is placed, devices for the infusion of the contrast agent and the drip infusion stand. If the motion of the components extends outside of the steady-state circumferential orbit, there can be dangerous contact with such external apparatuses, the subject being imaged or the operator.

There also was a desire that, prior to the precession, the image from one point on the precession orbit be observable and confirmable by fluoroscopy. That is, by setting the position from which a run is to start on the precession orbit, there was a desire that the angle from which the angiogram would be observed be confirmed by fluoroscopy.

It is the object of the present invention to solve the afore-described problems and to allow precession to take place safely and quickly.

Means for Solving the Problems

To achieve the afore-described objects, the present invention includes: an X-ray irradiation means; an X-ray image detection means; a first holding means for holding the X-ray irradiation means and the X-ray image detection means to oppose each other; a second holding means for holding the first holding means to be rotatable about a first axis; a first driving means for rotating the first holding means; a third holding means for holding the second holding means to be rotatable about a second axis that is orthogonal to the first axis; a second driving means for rotating the second holding means; a drive control means for controlling the driving speed of the first driving means and the second driving means, the drive control means controlling the first driving means and the second driving means so that:

(A), in a steady-state, either the first holding means or the second holding means is rotated with an angular velocity of a·sin(t) while the other holding means is rotated with an angular velocity of b·cos(t) so that the X-ray irradiation means and the X-ray detection means engage in a precession motion along either a circular or an elliptical orbit; and (B) the one or the other holding means is made to engage in a running time, $\Delta T_1$, with an angular velocity of f(t) starting from an initial angle of $\phi_1$ while the other holding means is made to engage in a running time, $\Delta T_2$, with an angular velocity of g(t) starting from an initial angle of $\phi_2$ so that, assuming that a steady-state is reached at time t=T, all of the following equations are satisfied with respect to the parameter $\Delta T$:

$$\int_{t=T-\Delta T_1}^{T} f(t)dt = \int_{t=T-\Delta T}^{T} a \cdot \sin(t)dt \quad \text{Equation 2}$$

$$\int_{t=T-\Delta T_2}^{T} g(t)dt = \int_{t=T-\Delta T}^{T} b \cdot \cos(t)dt$$

$$f(T) = a \cdot \sin(T), \, f(T - \Delta T_1) = 0$$

$$g(T) = b \cdot \cos(T), \, g(T - \Delta T_2) = 0$$

$$\left| \frac{d}{dt} f(t) \right| \leq |a| \, (T - \Delta T_1 \leq t \leq T)$$

$$\left| \frac{d}{dt} g(t) \right| \leq |b| \, (T - \Delta T_2 \leq t \leq T)$$

$$\phi_1 = -a \cdot \cos(T - \Delta T)$$

$$\phi_2 = b \cdot \sin(T - \Delta T)$$

Operation

The technical significance of satisfying the relationships of equation 2 is as follows.

(1) Technical significance of the integral value of f(t) and g(t)

The integral value of f(t) represents the angle by which one of the aforesaid holding means rotates during a running period from time t=T−$\Delta T_1$ to T. Similarly, the integral value of g(t) represents the angle by which the other aforesaid holding means rotates during a running period from time $t=T-\Delta T_2$ to T.

(2) Technical significance of the integral values of $a \cdot \sin(t)$ and $b \cdot \cos(t)$ and $\Delta T$.

Assuming that one or the other of aforesaid holding means engages in a steady-state rotation for the duration from time $t=T-\Delta T$ to T, the integral value of $a \cdot \sin(t)$ represents the angle by which one or the other of the holding means rotates. Similarly, the integral value of $b \cdot \cos(t)$ represents the angle by which one of the holding means rotates assuming that the other aforesaid holding means engages in a steady-state rotation for the duration from time $t=T-\Delta T$ to T.

(3) Technical significance of the integral values of aforesaid (1) and (2) being equal This is analogous to using velocity profiles f(t) and g(t) for respective durations $\Delta T_1$ and $\Delta T_2$ to rotate one or the other holding means and the other holding means by an angle which they would have rotated had they been simultaneously and instantaneously rotated by a steady-state angular velocity for a period of $\Delta T$.

(4) Technical significance of $f(T-\Delta T_1)=0$, $f(T)=a \cdot \sin(T)$, $g(T-\Delta T_2)=0$ and $g(t)=b \cdot \cos(T)$ They represent the fact that the angular velocity at the start of a run is 0 and that the angular velocity at the time of completion of a run (t=T) is the same as the steady-state angular velocity.

(5) Technical significance of the absolute values of the differential values of f(t) and g(t) being less than the absolute values of a and b These conditions mean that the rate of acceleration during a running period do not exceed the maximum rate of acceleration during steady-state.

(6) Technical significance of $\phi_1 = -a \cdot \cos(T-\Delta T)$ and $\phi_2 = b \cdot \sin(T-\Delta T)$ These conditions mean that a running period angle is on a circular or elliptical orbit and that the angle at time T is such that it would be on a circumferential orbit for the angular velocity at that point in time.

If all of the above requirements (1) through (6) are met, a run begins from a circular or an elliptical orbit and the run is performed using a rate of acceleration that does not exceed the maximum steady-state rate of acceleration, and a steady-state precession starts at time T.

Furthermore, the present invention is characterized by the drive control means controlling the first driving means and the second driving means so that, during the running period, the X-ray irradiation means and the X-ray detection means move inside the steady-state circular or elliptical orbit.

Effects of the Invention

As clear from the foregoing, the present invention suppresses the generation of vibration during a running period to a steady-state precession, thereby eliminating the effects of vibration on the captured images and reducing the fear felt by the subject being imaged. Still furthermore, the present invention minimizes the risk of contact between the X-ray diagnostic device and objects located near it such as the top board where the subject is placed, the devices required for injecting the contrast agent into the subject, the infusion stand and other various apparatuses, the subject and the operator.

DESCRIPTION OF THE NUMERICAL REFERENCES

Figure 1:
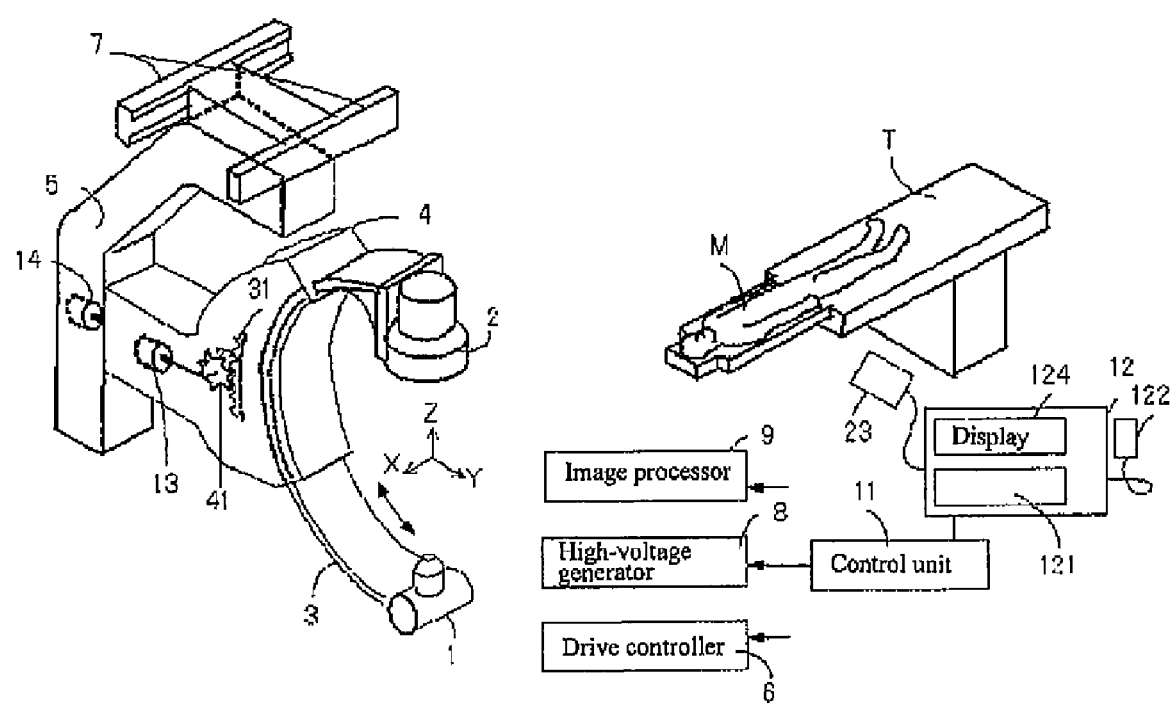
FIG. 1 shows a schematic view of the configuration of an X-ray diagnostic device according to the present invention.

1. X-ray tube
2. X-ray image detection means
3. C-arm
4. Holding means
5. Holding means
6. Drive controller
7. Ceiling rails
8. Voltage generator
9. Image processing device
10. Monitor
11. Control unit
12. Operation panel
121. Input device
122. photograph switch
123. Foot switch
124. Display device
13. Servo motor
14. Servo motor
41. Pinion gear
31. Rack
M. Subject
T. Top board
101. X-ray irradiation means
102. X-ray image detection means
103. C-arm
104. Holding means
105. Holding means
113. Rotation driving means
114. Rotation driving means
106. Drive control means

BEST MODE FOR PRACTICING THE INVENTION

Embodiments of the present invention are described next with reference to drawings.

Embodiment 1

FIG. 1 shows a schematic view of the X-ray diagnostic device according to the present invention, the X-ray diagnostic device comprising: C-arm 3 which holds X-ray irradiation means 1 and X-ray image detection means 2 to oppose each other; holding means 4 which holds C-arm 3 so that the C-arm can slidingly rotate; holding means 5 which holds holding means 4 so that holding means 4 can rotate about the Y-axis; servo motor 13 that slidably rotates C-arm 3; and servo motor 14 that rotates holding means 4. The rotational axis of servo motor 13 is coupled with pinion gear 41 that is disposed on the holding means 4, and the pinion gear 41 meshes with rack 31 that is disposed on the C-arm 3. Given the configuration, the rotation of servo motor 13 causes pinion gear 41 to rotate which in turn causes C-arm 3 to undergo a sliding movement. Drive controller 6 that controls servo motors 13 and 14 are also provided.

Servo motors 13 and 14 serve as the rotation driving means in the present invention. The drive controller 6 serves as the drive control means in the present invention. However, with the present invention, the rotation driving means is not limited to a servo motor and can be configured from any motor, for example, a simple DC motor or an AC motor that does not have a built-in feedback control, that can drive the C-arm 3 or holding means 4 at a specified angular velocity. However, if a servo motor is used, precession can be performed with accuracy.

The holding means 5 is held so that it can engage in a translational motion with respect to ceiling rails 7. The fact that the holding means 5 is held by ceiling rails 7 is not a limitation, and the holding means 5 may be placed on the floor, or may be positioned on the floor or on the ceiling rails via some other parts. In particular, it is acceptable to provide a holding means that holds the holding means 5 so that the holding means 5 is rotatable about rotational axis Z which is orthogonal to the rotational axes X and Y and to mount the holding means to aforesaid ceiling rails 7 or the floor.

On the other hand, the subject M being imaged is placed on top board T, and the top board T or the C-arm 3 is moved so that region of interest of the subject M being imaged is positioned between the X-ray irradiation means 1 and the X-ray image detection means 2. Furthermore, the X-ray diagnostic device comprises a high voltage generator 8 that supplies a high voltage satisfying certain predetermined conditions to the X-ray irradiation means 1, an image processing device 9 that processes image signals output by the X-ray image detection means 2 and generates images and a monitor 10 (not illustrated) that displays the generated images.

Furthermore, the X-ray diagnostic device comprises control unit 11 which issues instructions to the drive controller 6, high voltage generator 8 and image processing device 9. Connected to the control unit 11 is an operation panel 12 which comprises: an input device 121 used for purposes such as setting the image classification and the X-ray conditions and positioning the C-arm 3; photograph switch 122 for starting the X-ray imaging; foot switch 123 for performing X-ray fluoroscopy; and display device 124 for displaying various information such as the X-ray conditions.

Disposed on the input device 121 is a switch for moving to the initial position for precession. When the switch is pressed, control unit 11 issues an instruction to drive controller 6 so that the C-arm 3 moves to the initial position for precession registered in advance. The drive controller 6 that receives the instruction issues an instruction to servo motors 13 and 14 so that the C-arm 3 moves to the initial position.

The operator operates the input device 121 and selects precession mode as the image classification. The X-ray conditions (fluoroscopy conditions, imaging condition) are then set. After that, movement switches on the input device 121 for moving to the initial position for precession are operated to move the C-arm 3 to the initial position.

When the operator operates the foot switch 123 in this state, the control unit 11 issues an X-ray irradiation command to the high voltage generator 8. Together with that, an instruction is issued to the image processing device 9 to process the image signals that are output by the X-ray image detection means 2 and generate images. The high voltage generator 8 outputs to X-ray irradiation means 1 a high voltage that is commensurate for the fluoroscopic conditions. The X-ray irradiation means 1 irradiates an X-ray that corresponds to the high voltage. The X-ray that is radiated passes through the region of interest of subject M and becomes incident to the X-ray image detection means 2. The X-ray image detection means 2 then outputs an image signal that corresponds to the incident X-ray. The image processing device 9 receives instructions from the control unit 11, processes the image signals that are output by the X-ray image detection means 2 and generates images which are displayed on monitor 10.

The operator checks the fluoroscopic image that is displayed on the monitor 10 to make sure that the region of interest is positioned near the center of the image, and if angiograms are to be viewed by infusing a contrast agent, the operator presses the photograph switch 122 to view the fluoroscopic images that are displayed on monitor 10 to make sure that the contrast agent has reached the general region of interest. When the photograph switch 122 is pressed, the control unit 11 issues a command to the drive controller 6 to start the precession.

Run Control

Figure 2:
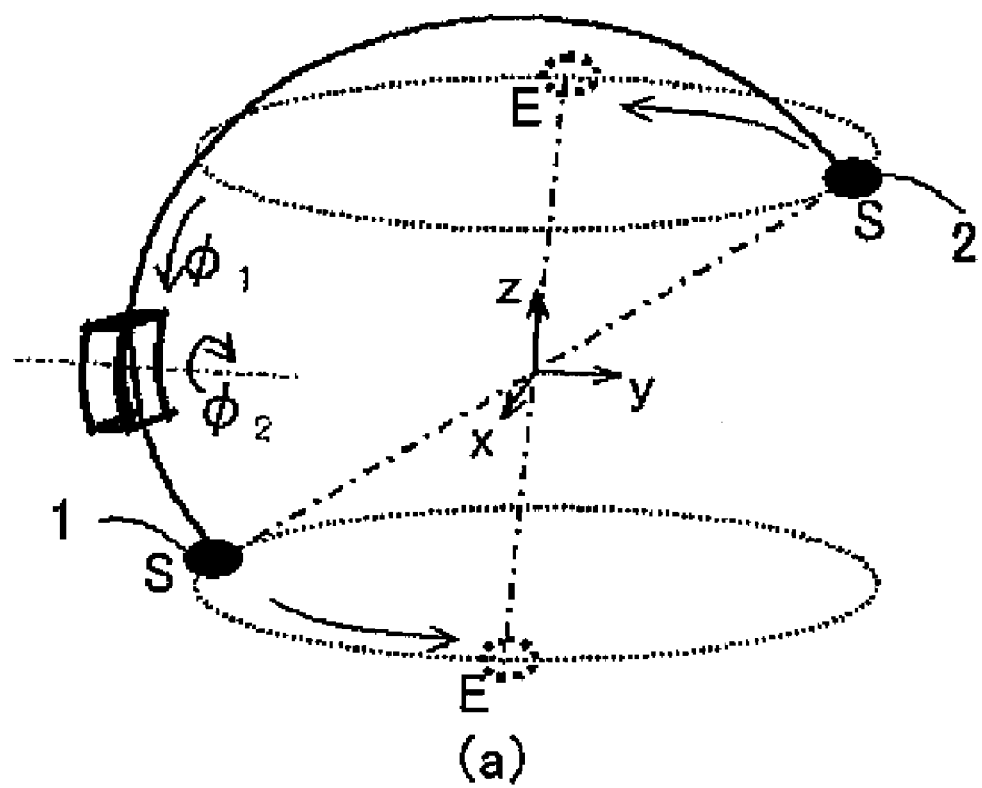
FIG. 2 is a schematic view describing the precession that occurs with the present invention.
Figure 2:
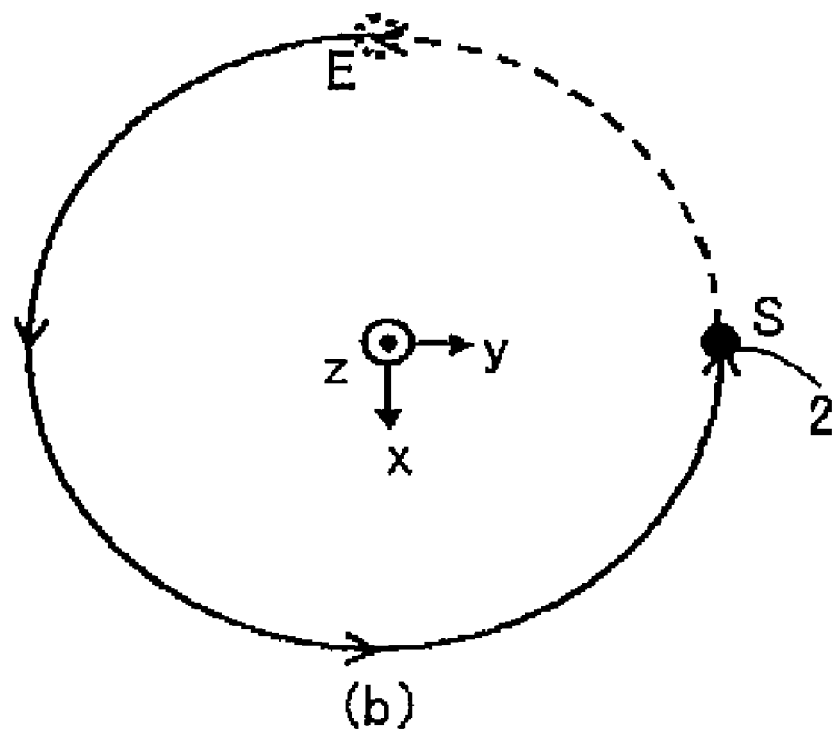

When the drive controller 6 receives an instruction from control unit 11, the drive controller 6 controls the servo motors 13 and 14 and starts the run. How the run is controlled is described in detail with reference to FIG. 2. FIG. 2(a) is a perspective view showing the path followed by the X-ray tube 1 and the X-ray image detector 2. FIG. 2(b) shows FIG. 2(a) as seen from the position direction along the Z-axis. In this particular coordinate system, the vector from X-ray tube 1 to the X-ray image detector 2 coincides with the Z-axis when the rotational angle $\phi_1$ of the C-arm 3 is 0 and the rotational angle $\phi_2$ of the holding means 4 is 0. The rotational angle $\phi_1$ of C-arm 3 is taken to be positive when the rotation is clockwise with respect to the X-axis (the direction of the arrow for $\phi_1$ in the figure). The rotational angle $\phi_2$ of the holding means 4 is taken to be positive when the rotation is counter-clockwise with respect to the Y-axis (the direction of the arrow for $\phi_2$ in the figure).

(i) Determination of the Initial Position S and the Steady-State Start Position E The initial position (S in FIG. 2(a)) of the C-arm 3 and the holding means 4 is set to be $\phi 0_{S1} = -\pi/6$ (−30 degrees) and $\phi 0_{S2} = 0$. Assuming that the distance equivalent to ¼ of one full period in steady-state is used as the running length, this requires that the C-arm 3 be rotated by $\pi/6$ and the holding means 4 be rotated by $\pi/6$ by the time the position (position E in FIG. 2(a), $\phi 0_{E1} = 0$, $\phi_{E2} = \pi/6$) for starting a steady-state operation is reached. The ratio of the major axis to the minor axis of the elliptical orbit or the circular orbit of the X-ray irradiation means 1 and 2-dimensional radiation detector 2 which is determined by such factors as the initial position is analogous to the ratio of a to b in the present invention. With the present embodiment, $\phi 0_{S1} 32\ \pi/6$ corresponds to a of the present invention and $\phi 0_{E2} = \pi/6$ corresponds to b of the present invention. This means that X-ray irradiation means 1 and two-dimensional radiation detector 2 move along a circular orbit.

(ii) Calculation of the Time Required for a Run from the Running Length

Letting f(t) represent the velocity function of C-arm 3, the following equation holds if C-arm 3 is moved by time T over a time duration $\Delta T_1$.

$$\int_{t=T-\Delta T_1}^{T} f(t)\,dt = \frac{\pi}{6} = \int_{t=T-\Delta T}^{T} \frac{\pi}{6} \cdot \sin(t)\,dt \qquad \text{Equation 4}$$

Furthermore, letting g(t) represent the velocity function of holding means 4, the following equation holds if holding means 4 is moved by time T over a time duration $\Delta T_2$.

$$\int_{t=T-\Delta T_2}^{T} g(t)\,dt = \frac{\pi}{6} = \int_{t=T-\Delta T}^{T} \frac{\pi}{6} \cdot \cos(t)\,dt \qquad \text{Equation 5}$$

The unit used for t according to the present invention is not necessarily "second" but that which was normalized in accordance with the required time of $2\pi$ for making a positional procession cycle in steady state. Since the afore-described setting is analogous to using the distance corresponding to ¼ of the time of one period in a steady-state as a running length, $\Delta T$ becomes equal to $\pi/2$.

(ii) Calculation of the Time Required for a Run from a Running Length

Figure 3:
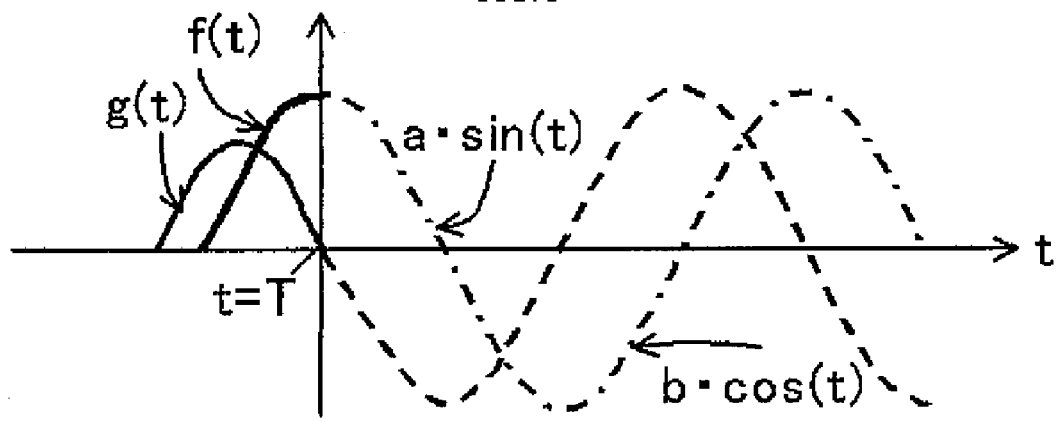
FIG. 3 is a graph showing a running period in one embodiment of the present invention.

The functions f(t) and g(t) in aforesaid equations 4 and 5 may be functions that are fixed for each and every circumstance or may be functions that change with the circumstances. The present embodiment uses functions that are shown in FIG. 3. These functions satisfy the following condition, namely, that the change in speed during the running period not exceed the respective maximum rate of acceleration. This condition eliminates the detrimental effects on the images of the system's vibration and provides a sense of security to the subject being imaged.

$$\left|\frac{d}{dt}f(t)\right| \leq |a| \quad (T - \Delta T_1 \leq t \leq T) \qquad \text{Equation 6}$$

$$\left|\frac{d}{dt}g(t)\right| \leq |b| \quad (T - \Delta T_2 \leq t \leq T)$$

In this case, the values of $\Delta T_1$ and $\Delta T_2$ that satisfy these equations are calculated. Drive controller 6 uses the calculated values of $\Delta T_1$ and $\Delta T_2$ as a basis for the speed instructions that are issued to servo motors 13 and 14.

Figure 4:
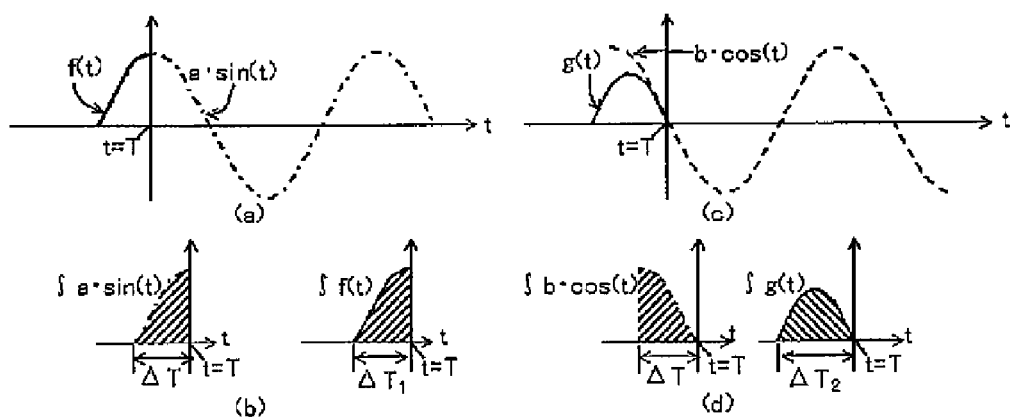
FIG. 4 shows graphs depicting the relationship between the rotational angles during a running period in one embodiment of the present invention.

FIG. 4 shows the relationship between angular velocity and rotational angle during the running period when the afore-described control is implemented. FIG. 4(*a*) shows the change in the rotational angular velocity of C-arm 3. In the figure, the dotted line shows the steady-state velocity, and f(t) shows the velocity during the running period. The left figure in FIG. 4(*b*) shows the angle of rotation during the running period as an integral value (hatched line area). The right figure in FIG. 4(*b*) shows the angle as an integral value (hatched line area) when driven using the same rotational angular velocity as in the steady-state. The function f(t) is decided so that the areas of the hatched line regions shown in the left and right in FIG. 4(*b*) are equal. With the present embodiment, the rotational angular velocity of C-arm 3 during the running period is the same as that during the steady-state. Similarly, FIGS. 4(*c*) and (*d*) show the angular velocity and rotational angle of the holding means 4 during the running period. The function g(t) is determined so that the area of the hatched line regions shown to the left and right in FIG. 4(*b*) is the same. With the present embodiment, g(t)=b/2 cos(t+$\Delta T_2$).

Position E shown in FIG. 2 is reached at time t=T. With the present embodiment, the holding means 4 is first made to start rotating with a velocity of g(t) to be followed by the rotation of C-arm 3 with a velocity of f(t).

Steady-State Operation

Simultaneous with the completion of the running operation, the control unit 11 issues an X-ray irradiation instruction to the high voltage generator 8. At the same time, an instruction is issued to the image processing device 9 to process the image signal that is output by the X-ray image detection means 2 and to generate images. By this time, the C-arm 3 would have completed its run and is moving at a steady-state along a precession orbit. The high voltage generator 8 applies a high voltage to X-ray tube 1 in accordance with pre-determined conditions, causing the X-ray tube 1 to radiate X-rays. The radiated X-rays pass through the region of interest of the subject M and becomes incident to the X-ray image detection means 2 which outputs image signals that correspond to the incident X-rays. The image processing device 9 receives instructions from the control unit 11 and processes the image signals that are output by the X-ray image detection means 2 and generates images which are displayed on monitor 10. Furthermore, the image processing device 9 incorporates an image storage means 91 where the series of image groups that are collected are recorded. Since the series of afore-described operations are continuously performed and accompanied with a steady-state precession that is caused by C-arm 3 and holding means 4 being driven by servo motors 13 and 14, three-dimensional moving images are displayed on the monitor 10. As for the timing for issuing an X-ray radiation command from the control unit 11 to the high voltage generator 8, this does not need to be simultaneous with the completion of the running operation and may instead be before or after that. Furthermore, outputting a signal (so-called ready signal) required for preheating the X-ray tube 1 when a run is started is desirable since the X-ray radiation can be immediately started after the X-ray radiation command is issued.

(Image Completion)

When the operator stops the input from the photograph switch 122, the control unit 11 issues an instruction to the high voltage generator 8 to stop the radiation of X-rays. Also, an instruction to stop collecting images is issued to the image processing device 9. Furthermore, an instruction is issued to the drive control means 6 to stop the C-arm. It is desirable for the C-arm to be stopped using a gradual deceleration just as during the afore-described run control. However, even if the device were to vibrate, there is no need for the decrease in speed to be performed at the same general rate of acceleration as during the run so long as the vibration converges by the next run. In fact, it is desirable for the C-arm to be stopped as quickly as possible without causing a sense of fear in the subject M. However, in the interest of safety, it is no different from the run in that it is desirable to control the rotation speed so that the X-ray tube 1 or the X-ray image detector 2 does not move outside of the circumferential orbit.

Figure 5:
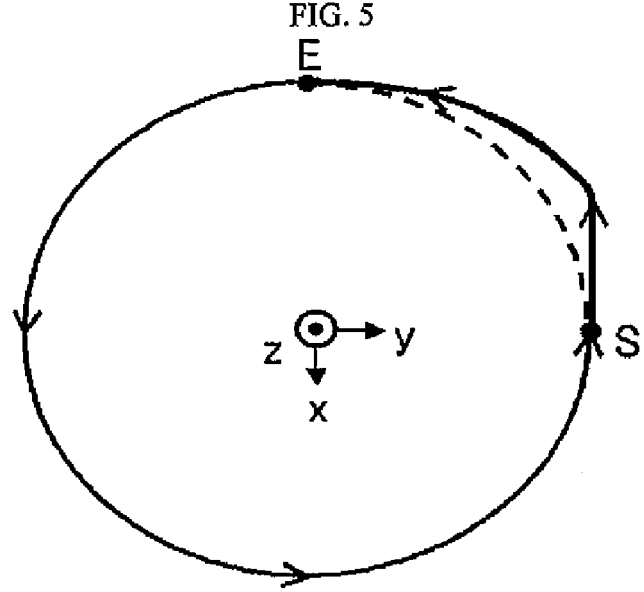
FIG. 5 shows the path of movement of the X-ray detection means in one embodiment of the present invention.

FIG. 5 shows the orbit of the X-ray tube 1 on the X-Y plane when the afore-described control is performed. Because the holding means 4 was rotated first, the X-ray tube 1 moves along a path that is located outside of the steady-state elliptical orbit. This presents the problem of interference with infusion stands, electrocardiograph device or devices for the infusion of the contrast agent that may be positioned nearby. For this reason, another embodiment (embodiment 2) is described next where the device is controlled so that the path of motion occurs along inside the circular or elliptical orbit.

Embodiment 2

Since the configuration of drive controller 6 other than the running function is the same as that of embodiment 1, it's description is omitted here.

(ii) Calculation of the Time Required for a Run from a Running Length

Figure 6:
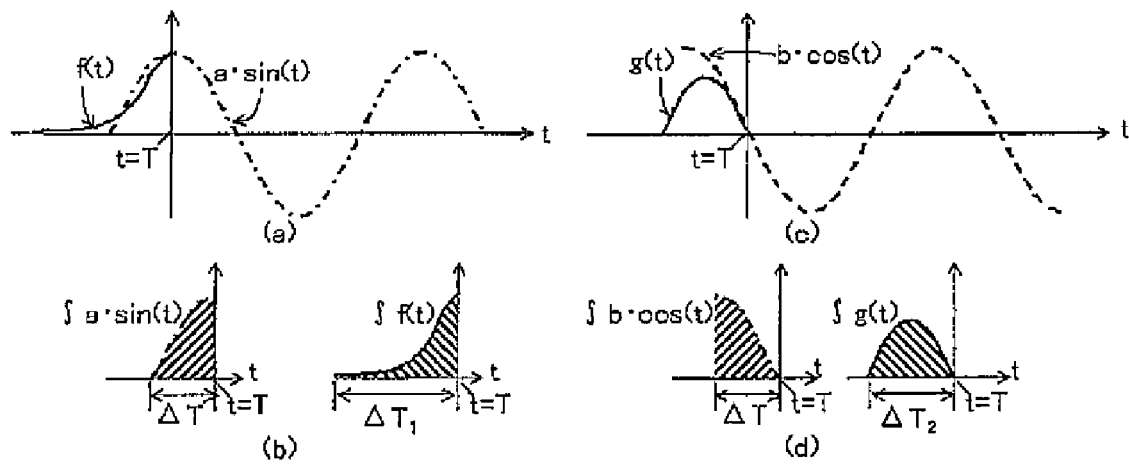
FIG. 6 shows graphs depicting the relationship between the rotational angles during a running period in another embodiment of the present invention.
Figure 7:
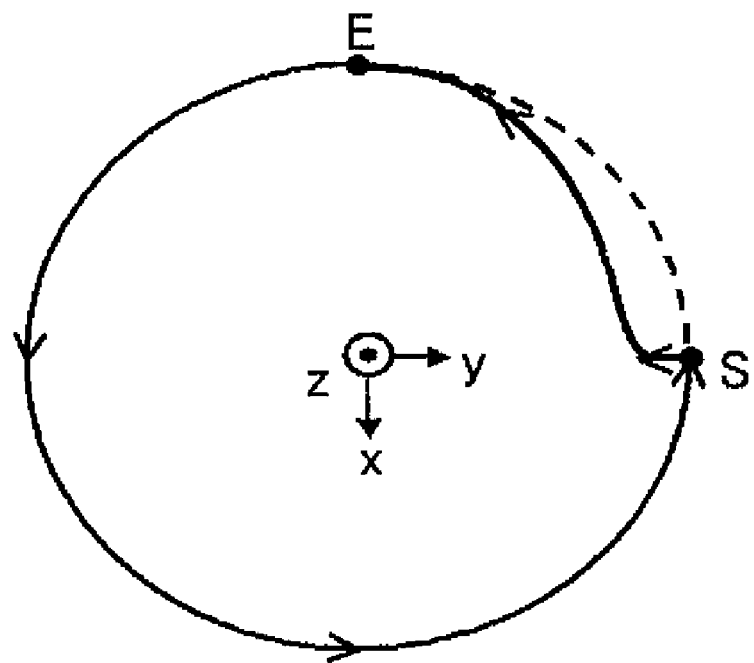
FIG. 7 shows the path of movement of the X-ray detection means in the another embodiment of the present invention.
Figure 8:
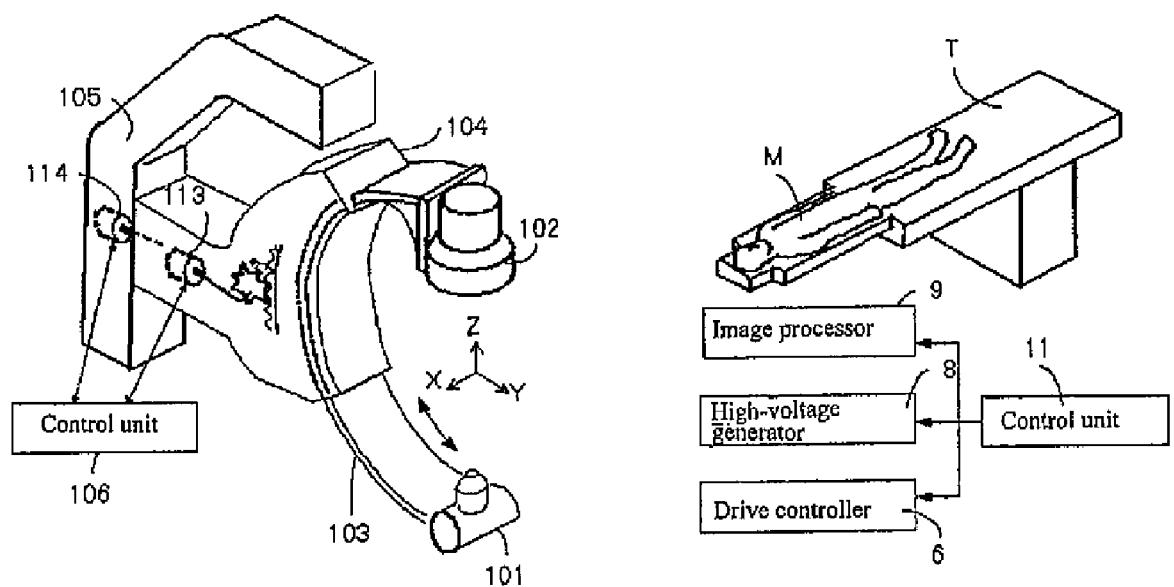
FIG. 8 shows a schematic view of the configuration of previous X-ray diagnostic device.
Figure 9:
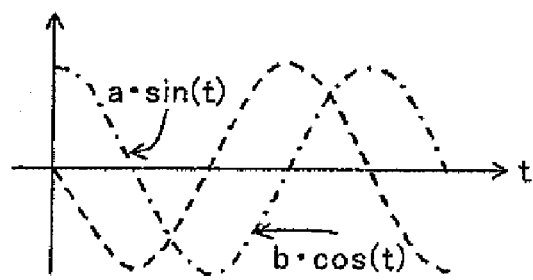
FIG. 9 is a graph showing the steady-state speed for the precession in the previous technology.

Functions f(t) and g(t) shown in equations 4 and 5 above may be fixed for all circumstances or may be variable depending on circumstances. With the present embodiment, functions such as those shown in FIG. 6 are used. The meaning of the individual graphs shown in FIG. 6 is the same as in FIG. 4. The respective functions satisfy the following conditions. To explain, while satisfying the condition that the change in velocity during the running period not exceed the respective maximum rates of acceleration, C-arm 3 is rotated first using the velocity function f(t) and the holding means 4 is then rotated using the velocity function g(t). This eliminates the detrimental effects on the images of the vibration in the device as shown in FIG. 7, and provides a sense of security to the subject being imaged. Furthermore, this allows the X-ray irradiation means 1 and two-dimensional radiation detector 2 to move during the running period inside the steady-state circumferential orbit.

Based on the calculated values of $\Delta T_1$ and $\Delta T_2$, the drive controller 6 issues a speed instruction to servo motors 13 and 14. FIG. 4 shows functions f(t) and g(t) superimposed on each other with the horizontal axis representing time t. Position E in FIG. 2 is reached at time t=T. With the present embodiment, since the value of $\Delta T_2$ is initially larger, holding means 4 is first rotated using a velocity function g(t) and is followed by C-arm 3 which rotates with a velocity function of f(t).

In this way, the present invention includes the implementation wherein the operation using the required rate of acceleration is achieved using different operation timings for the two axes. However, depending on functions f(t) and g(t) that are used, the operations can start at the same time.

What is claimed is:

1. An X-ray diagnostic device comprising:
an X-ray irradiation means;
an X-ray image detection means;
a first holding means for holding the X-ray irradiation means and the X-ray image detection means to oppose each other;
a second holding means for rotatably holding the first holding means about a first axis;
a first driving means for rotatably driving the first holding means;
a third holding means for rotatably holding the second holding means about a second axis that is orthogonal to the first axis;
a second driving means for rotatably driving the second holding means; and
a drive control means for controling the driving speed of the first driving means and the second driving means;
wherein the drive control means controls the first driving means and the second driving means so that:
(A) one of the holding means, either the first holding means or the second holding means, rotates in steady-state with an angular velocity of a·sin(t) and the other holding means rotates with an angular velocity of b·cos(t) so that the X-ray irradiation means and the X-ray detection means move in a precession motion along a circular or an elliptical orbit; and
(B) one of the holding means engages in a run time, $\Delta T_1$ from an initial angle $\phi_1$ using an angular velocity f(t) and the other holding means engages in a run time, $\Delta T_2$ from an initial angle $\phi_2$ using an angular velocity g(t) so that, assuming that a steady-state is reached at time t=T, all of the following equations are satisfied with respect to the parameter $\Delta T$:

$$\int_{t=T-\Delta T_1}^{T} f(t)dt = \int_{t=T-\Delta T}^{T} a \cdot \sin(t)dt \qquad \text{Equation 1}$$

$$\int_{t=T-\Delta T_2}^{T} g(t)dt = \int_{t=T-\Delta T}^{T} b \cdot \cos(t)dt$$

$$f(T) = a \cdot \sin(T), \ f(T - \Delta T_1) = 0$$

$$g(T) = b \cdot \cos(T), \ g(T - \Delta T_2) = 0$$

$$\left|\frac{d}{dt}f(t)\right| \le |a| \ (T - \Delta T_1 \le t \le T)$$

$$\left|\frac{d}{dt}g(t)\right| \le |b| \ (T - \Delta T_2 \le t \le T)$$

$$\phi_1 = -a \cdot \cos(T - \Delta T)$$

$$\phi_2 = b \cdot \sin(T - \Delta T),$$

wherein a and b are maximum angular velocities, t is time and $\Delta T$ is the time of rotation from angles $\phi_1$ and $\phi_2$ to reach an angle under a steady-state angular velocity based on a·sin(t) and b·cos(t).

2. The X-ray diagnostic device according to claim 1 wherein the drive control means controls the first driving means and the second driving means so that, during the running period, the X-ray irradiation means and the X-ray detection means move along a path that is inside the circular or elliptical orbit in steady-state.

* * * * *